(12) United States Patent
Clunet-Coste et al.

(10) Patent No.: US 9,033,708 B2
(45) Date of Patent: May 19, 2015

(54) IMPLANT-SUPPORTED BRACED DENTAL BRIDGE ARMATURE MADE FROM COMPOSITE MATERIAL, AND METHOD FOR MANUFACTURING THE ARMATURE

(71) Applicants: Bruno Clunet-Coste, Saint Etienne de Crossey (FR); Bernard Maneuf, Voiron (FR); Andre Collombin, Voiron (FR); Raymond Monette, Le Gardeur (CA)

(72) Inventors: Bruno Clunet-Coste, Saint Etienne de Crossey (FR); Bernard Maneuf, Voiron (FR); Andre Collombin, Voiron (FR); Raymond Monette, Le Gardeur (CA)

( * ) Notice: Subject to any disclaimer, the term of this patent is extended or adjusted under 35 U.S.C. 154(b) by 0 days.

(21) Appl. No.: 13/849,711

(22) Filed: Mar. 25, 2013

(65) Prior Publication Data

US 2013/0252203 A1 Sep. 26, 2013

(30) Foreign Application Priority Data

Mar. 23, 2012 (FR) ..................................... 12 00874

(51) Int. Cl.
*A61C 8/00* (2006.01)
*A61C 13/00* (2006.01)

(52) U.S. Cl.
CPC .............. *A61C 8/0009* (2013.01); *A61C 8/0048* (2013.01); *A61C 13/0003* (2013.01); *A61C 8/0068* (2013.01)

(58) Field of Classification Search
CPC .............. A61C 13/0003; A61C 8/0009; A61C 8/0048; A61C 8/0068
USPC ................................................ 433/167–175
See application file for complete search history.

(56) References Cited

U.S. PATENT DOCUMENTS

| | | | | |
|---|---|---|---|---|
| 2,755,552 A * | 7/1956 | Brandau | | 433/215 |
| 2,793,436 A | 5/1957 | Gotlib | | |
| 2,929,143 A * | 3/1960 | Vahe | | 433/167 |
| 4,370,134 A * | 1/1983 | Roberts | | 433/173 |
| 5,064,374 A * | 11/1991 | Lundgren | | 433/173 |
| 5,176,951 A * | 1/1993 | Rudo | | 442/220 |
| 5,921,778 A * | 7/1999 | Karmaker et al. | | 433/215 |
| 6,010,337 A | 1/2000 | Billet et al. | | |
| 6,030,220 A * | 2/2000 | Karmaker et al. | | 433/215 |
| 6,039,569 A | 3/2000 | Prasad et al. | | |
| 6,056,547 A * | 5/2000 | Names | | 433/173 |
| 6,186,790 B1 * | 2/2001 | Karmaker et al. | | 433/215 |
| 6,381,989 B1 * | 5/2002 | Karmaker et al. | | 65/384 |
| 6,655,962 B1 * | 12/2003 | Kennard | | 433/174 |
| 6,846,181 B2 * | 1/2005 | Karmaker et al. | | 433/212.1 |
| 7,235,290 B2 * | 6/2007 | Vallittu et al. | | 428/296.7 |

(Continued)

FOREIGN PATENT DOCUMENTS

EP 0 292 026 11/1988
EP 0 974 310 A2 1/2000

(Continued)

*Primary Examiner* — Cris L Rodriguez
*Assistant Examiner* — Mirayda A Aponte
(74) *Attorney, Agent, or Firm* — Oliff PLC

(57) ABSTRACT

A dental bridge armature designed to be screw-fastened onto dental implants, the dental bridge armature having reinforcing elements formed by long fibers pre-impregnated with photo-polymerizable resin which are either woven or in bundles. The reinforcing elements are in the form of a fibrous framework including a main brace and base reinforcing elements wound around a series of implant abutments screwed onto the implants. Secondary braces are also wound around the main brace and the base reinforcing elements. The braces form an angle between 15° and 85° with the base reinforcing elements. The armature is then included in a PMMA coating resin by a pressing or injection technique.

8 Claims, 4 Drawing Sheets

(56) References Cited

U.S. PATENT DOCUMENTS

| | | | |
|---|---|---|---|
| 7,673,550 B2 * | 3/2010 | Karmaker et al. | 87/1 |
| 7,708,557 B2 * | 5/2010 | Rubbert | 433/173 |
| 2004/0018469 A1 * | 1/2004 | Summers | 433/173 |
| 2005/0277089 A1 * | 12/2005 | Brajnovic | 433/167 |
| 2006/0286502 A1 * | 12/2006 | Shor | 433/26 |
| 2009/0007817 A1 * | 1/2009 | Branjnovic | 106/35 |
| 2012/0308959 A1 * | 12/2012 | Vaidyaselvan | 433/172 |
| 2013/0017510 A1 * | 1/2013 | Rudo | 433/172 |

FOREIGN PATENT DOCUMENTS

| | | |
|---|---|---|
| FR | 2 588 181 | 4/1987 |
| FR | 2 939 636 | 6/2010 |
| FR | 2939636 A1 * | 6/2010 |
| WO | WO 02/30647 A2 | 4/2002 |
| WO | WO 0230647 A2 * | 4/2002 |

* cited by examiner ly made from a metal or from other aesthetic compact materials such as PMMA resin, or from ceramic, lithium disilicate ceramic, ceramics on armatures on zirconium oxides. Composites charged with various particles can also be used.

IMPLANT-SUPPORTED BRACED DENTAL BRIDGE ARMATURE MADE FROM COMPOSITE MATERIAL, AND METHOD FOR MANUFACTURING THE ARMATURE

BACKGROUND OF THE INVENTION

The invention relates to an armature of an implant-supported dental bridge in the form of a three-dimensional framework formed by elements made from photo-polymerizable pre-impregnated composite material the base of which is constituted by long fibres and particles, and designed to reinforce the body of dental resin bridges, said reinforcements being oriented such as to withstand functional stresses.

STATE OF THE ART

The document U.S. Pat. No. 2,755,552 describes reinforcements constituted by fibres to reinforce dental prostheses, crowns, and dental splints.

The document U.S. Pat. No. 2,793,436 relates to a system for reinforcing fixed or removable dental prostheses, with parallel or crossed fibres, or any other weaving texture, able to be colourless, transparent or opalescent.

The document FR 2,588,181 discloses the use of fibers made from composite materials to reinforce dental prostheses made from a totally or partially polymerized resin base, manufactured by pultrusion, injection, compression, molding, or transfer processes.

Known prostheses fixed onto teeth or dental implants are generally made from a metal or from other aesthetic compact materials such as PMMA resin, or from ceramic, lithium disilicate ceramic, ceramics on armatures on zirconium oxides. Composites charged with various particles can also be used.

When the aesthetic compact material has a fragile behaviour, it is known to support it by a more resistant armature which will provide it with the necessary support. This support armature is in general made from metal and is used in common practice in particular for manufacturing dental bridges, in particular when the latter are supported by dental implants. In FIG. 1 of the prior art, the technician then constitutes a beam (1) which joins the implants (2) and rigidifies the construction. The prosthetic teeth (3) are secured onto this beam (1), which has the function of securing the implants to one another and of supporting the fragile resin or ceramic, preventing the latter from sagging too much. The beam (1) may be coated by resin (4).

Other armatures made from fibre-reinforced composite material are also known:

the document U.S. Pat. No. 6,010,337 discloses a support shell made from fibre-reinforced composite material, said shell being formed by shaping on a laboratory model of a photo-polymerizable preform. The support shell is rigid, and its solid surface devoid of openings does not enable resin to be injected.

The document EP 0,292,026 discloses a reinforcement made from composite resin and from elongate continuous fibres designed to form a beam to join dental implants.

The document FR 2,939,636 describes a preform made from a composite material formed by resin, particles and fibres in the state prior to polymerization, designed to be formed on a laboratory model and to be integrated in a base plate of a dental prosthesis. It comprises a grid formed by a network of weft threads and warp threads coated in an impregnating resin, the central space between the meshes being devoid of fibres and of resin, and determining a surface of free spaces of more than 25% of the total surface of the grid. The weft threads are fixed onto the warp threads at the nodes of the network to enable the preform to be handled and to be formed on a laboratory model, without creepage of the impregnation resin into the spaces of the meshes.

In the case of implant-supported dental bridges, the teaching of the state of the art is to secure the implants by a beam, which is screw-fastened by screws (5, FIG. 1) onto the emergences (6) of the implants and supports the prosthetic teeth (3). The beam (1) provides the necessary rigidity to prevent too great a flexion of the resin (4) and breaking of the latter by fatigue or by excess flexion.

This rigid beam does however oppose physiological deformations of the osseous parts supporting the implants: for example, the jaw-bone, pulled towards the inside due to the oblique action of the raising muscles, is deformed in the course of the function inwards by up to 1.5 mm at molar level, simply when the mouth is opened.

Furthermore, the bone structure is different according to the sectors, resulting in a differential mobility of the osseous segments.

Such a known strengthening beam, by rigidifying the prosthesis, generates stress peaks on the implant-prosthetic structure joining system or on the implant itself, and this excessively stressed interface becomes the location of recurrent fractures or bone lysis leading to loss of osteointegration of the implant.

Finally, the rigidity of the implant-supported prostheses constitutes a cause of discomfort for the patient.

OBJECT OF THE INVENTION

A first object of the invention consists in providing an implant-supported bridge armature that does not rigidify the prosthesis and keeps its viscoelastic nature to resin.

The armature according to the invention comprises reinforcing elements formed by long fibres pre-impregnated with photo-polymerizable resin which are either woven or in bundles, said reinforcing elements being in the form of a three-dimensional fibrous framework comprising a main brace and base reinforcing elements, all wound around a series of implant abutments screw-fastened onto the implants. The ends of the main brace are advantageously inclined in the direction of the base reinforcing elements. Secondary braces are further wound around the main brace and base reinforcing elements.

A second object of the invention consists in providing an implant-supported bridge armature formed by a three-dimensional framework, which is filled with a coating resin and ensures the cohesion of the assembly and securing of the prosthetic teeth.

A third object of the invention is to provide a method for assembling the elements constituting the armature.

It is characterized by the following successive steps:

tension posts are fitted distally to the most distal implants,
implant abutments are fixed onto the implants,
a first reinforcing element, having first been tensed, is wound around the base of each implant abutment and is polymerized,
a second reinforcing element, having first been tensed, is wound around the base of each implant abutment and is polymerized,
a third reinforcing element forming a main brace passing through the apex of each implant abutment, having first been tensed, is wound and then polymerized, additional reinforcing elements forming secondary braces passing around the base reinforcement elements and elements of the main brace, are wound and then polymerized, and a coating resin is injected into the free spaces of the constituted fibrous armature.

BRIEF DESCRIPTION OF THE DRAWINGS

Other advantages and features will become more clearly apparent from the following description of a particular embodiment of the invention given for non-restrictive example purposes only and represented in the appended drawings, in which.

DETAILED DESCRIPTION OF THE INVENTION

Figure 1:
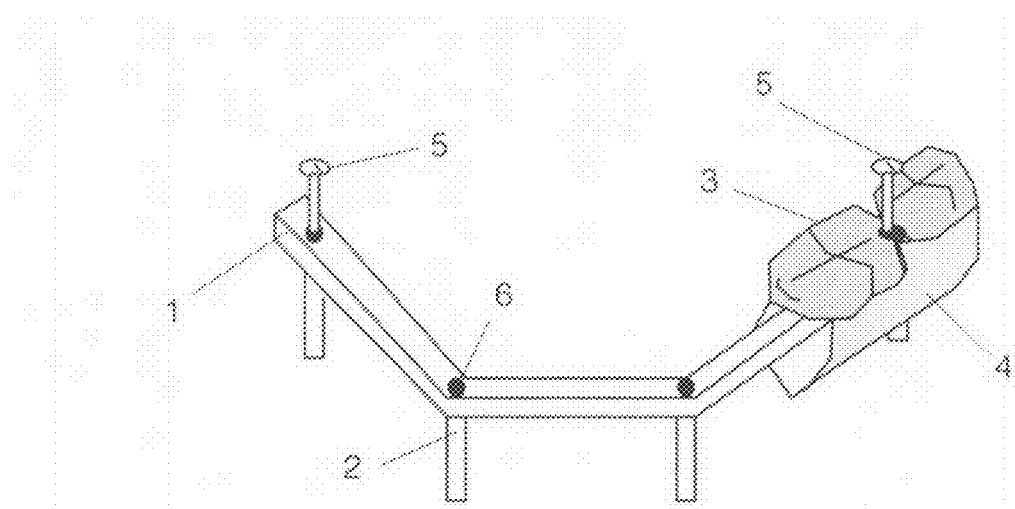
FIG. 1 is a schematic perspective view of an implant-supported dental bridge of the prior art.
Figure 2:
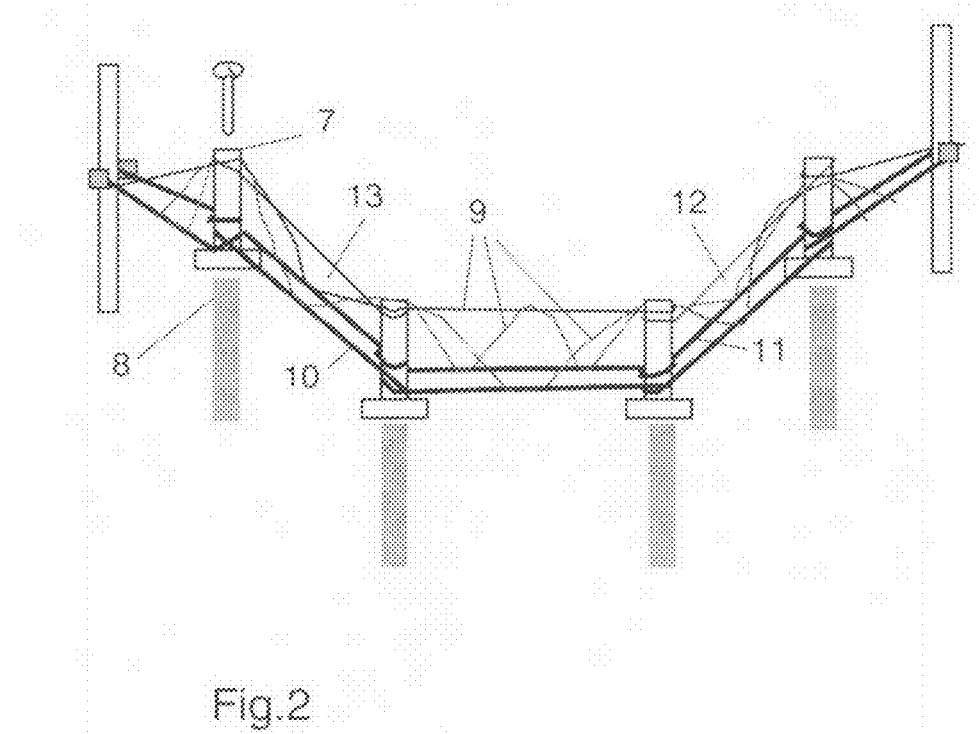
FIG. 2 represents a braced armature of an implant-supported dental bridge according to the invention.

With reference to FIG. 2, the bridge armature is formed by implant abutments 7 designed to be screwed onto the implant emergences 8. The implant abutments 7 support braces 9 made from photo-polymerizable composite material reinforced with long and continuous fibres, either woven or in bundles. These braces 9 secure in place decks 10, 11 also made from photo-polymerizable composite material reinforced with long and continuous fibres that are either woven or in bundles. Braces 9 and decks 10, 11 are independent from one another.

After braces 9 and decks 10, 11 have been fitted in place, spaces of framework 12 of the armature are free from fibres and impregnating resin. A resin 13 then fills these free spaces of the framework and renders the assembly solid to constitute a reinforced structure. Filling of the spaces by resin 13 enables the resistant elements of the framework of the armature to fulfil their role of reinforcement of the assembly and of solidity of the whole structure.

Fabricating such an armature made from composite material is a new way of manufacturing an implant-supported dental bridge, without having recourse to a rigid beam designed to support the resin constituting the bridge to prevent it from sagging. The resin coating the bridge is thus reinforced by a framework of continuous and oriented fibre-based elements, which resists the functional stresses, due to the presence of braces 9.

Figure 3:
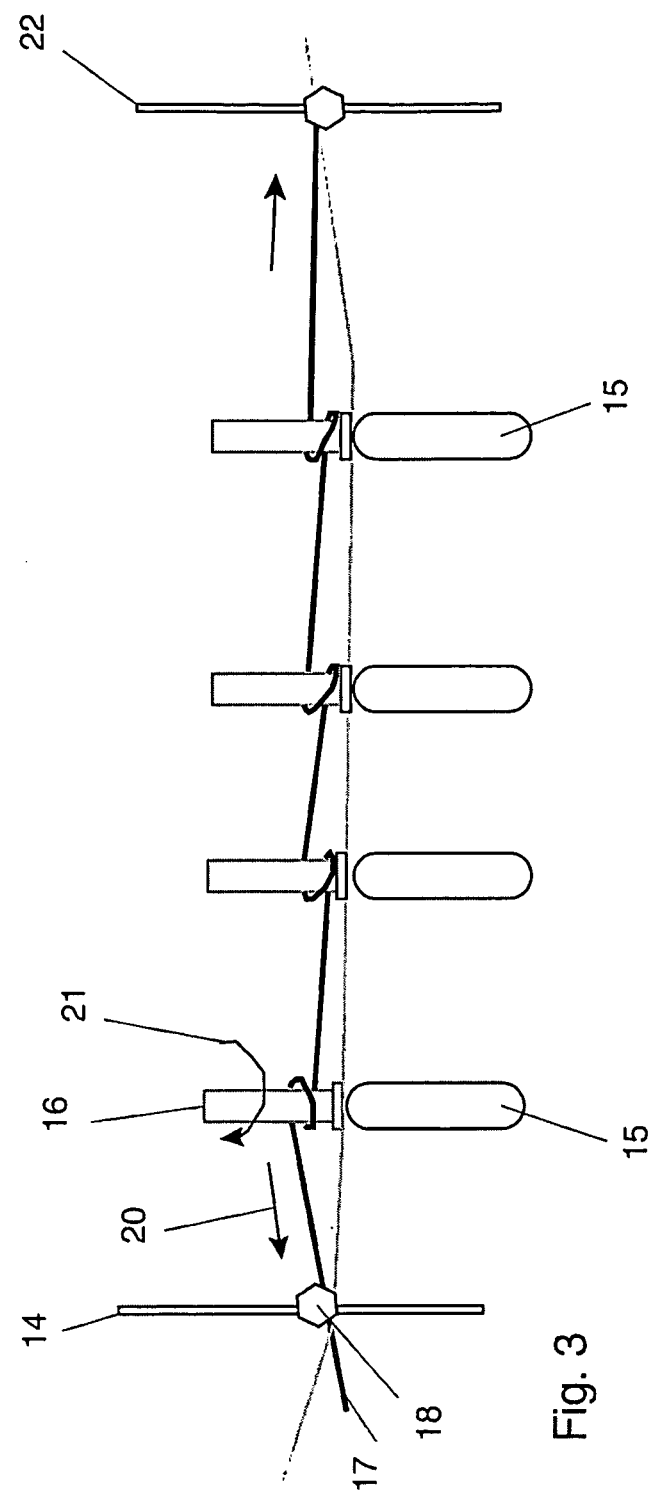
FIGS. 3 to 5 show the different steps of a preferred embodiment of the armature of FIG. 2.

Implementation of such a braced bridge is customised in dental prosthesis laboratories by means of the following method:

FIG. 3 shows a first step of a preferred embodiment of the armature. Two tension posts, one left 14 and one right 22, are installed distally to the most distal implants 15. The implants 15 are all provided with hollow implant abutments 16 designed to be screwed-fastened onto the implants. These implant abutments 16 are made from titanium, but can also be made from composite material. These implant abutments are affected to the tension of the reinforcement elements made from photo-polymerizable composite material reinforced with long fibres either woven or in bundles.

A first reinforcement element 17 is secured to the left-hand tension post 14 provided with retaining means 18. These retaining means 18 can be a drop of photo-polymerizable composite glue or a mechanical device. The first reinforcement element 17 is tensed (arrow 20) so as to join the nearest implant abutment 16 around which it is wound in the clockwise direction (arrow 21), and so on around the next implant abutment 16, and then the third and fourth abutments, until it finishes its path on the right-hand tension post 22.

Reinforcement element 17 is then photo-polymerized and remains hardened in the determined position to act as first vestibular base for the framework of the armature.

Figure 4:
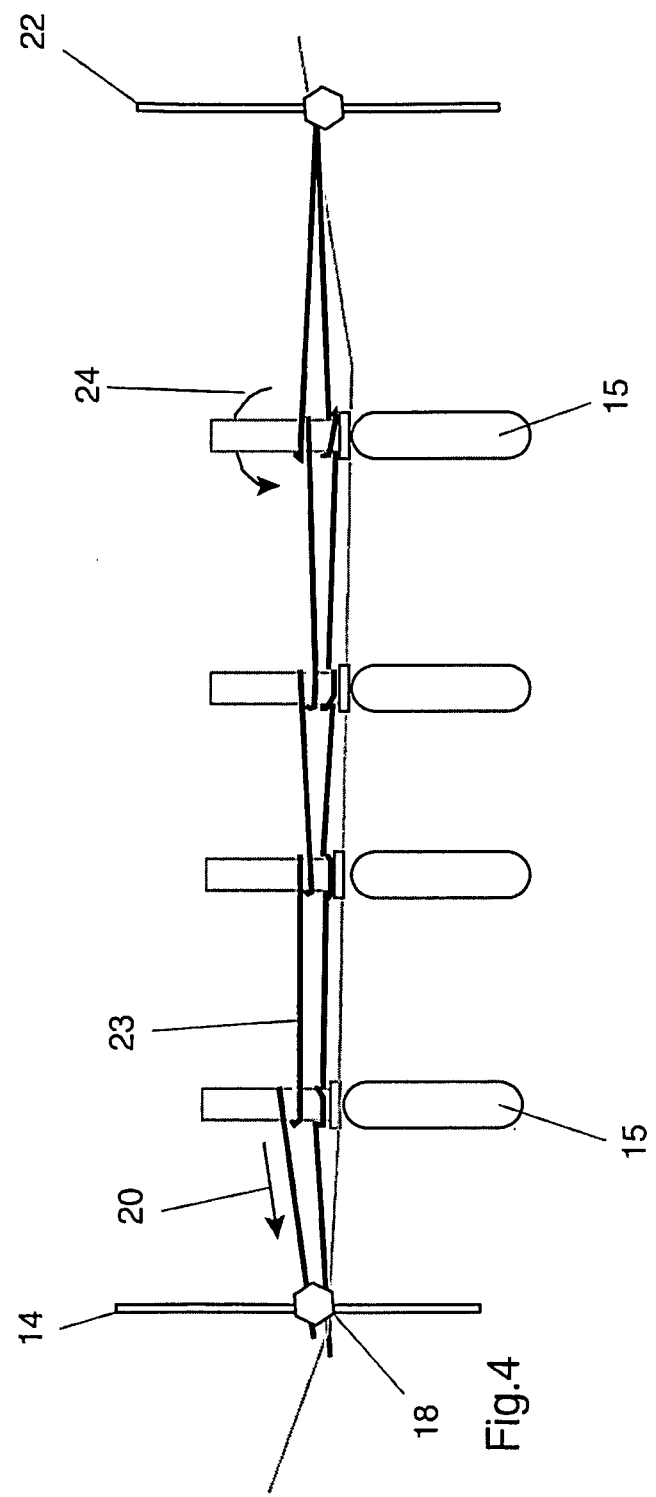

In FIG. 4, a second reinforcement element 23 is secured to the left-hand tension post 14 provided with retaining means 18. It is tensed (arrow 20) to join the nearest implant abutment 16 around which it is wound in the counter-clockwise direction (arrow 24), and so on around the next implant abutment, and then the third and fourth abutments, until it finishes its path on the right-hand tension post 22.

Second reinforcement element 23 is then photo-polymerized and remains hardened in the determined position to act as a second lingual or palatine base for the framework of the armature.

The two base elements 17, 23 are separated by a distance corresponding to the cross-section of the implant abutment.

Figure 5:
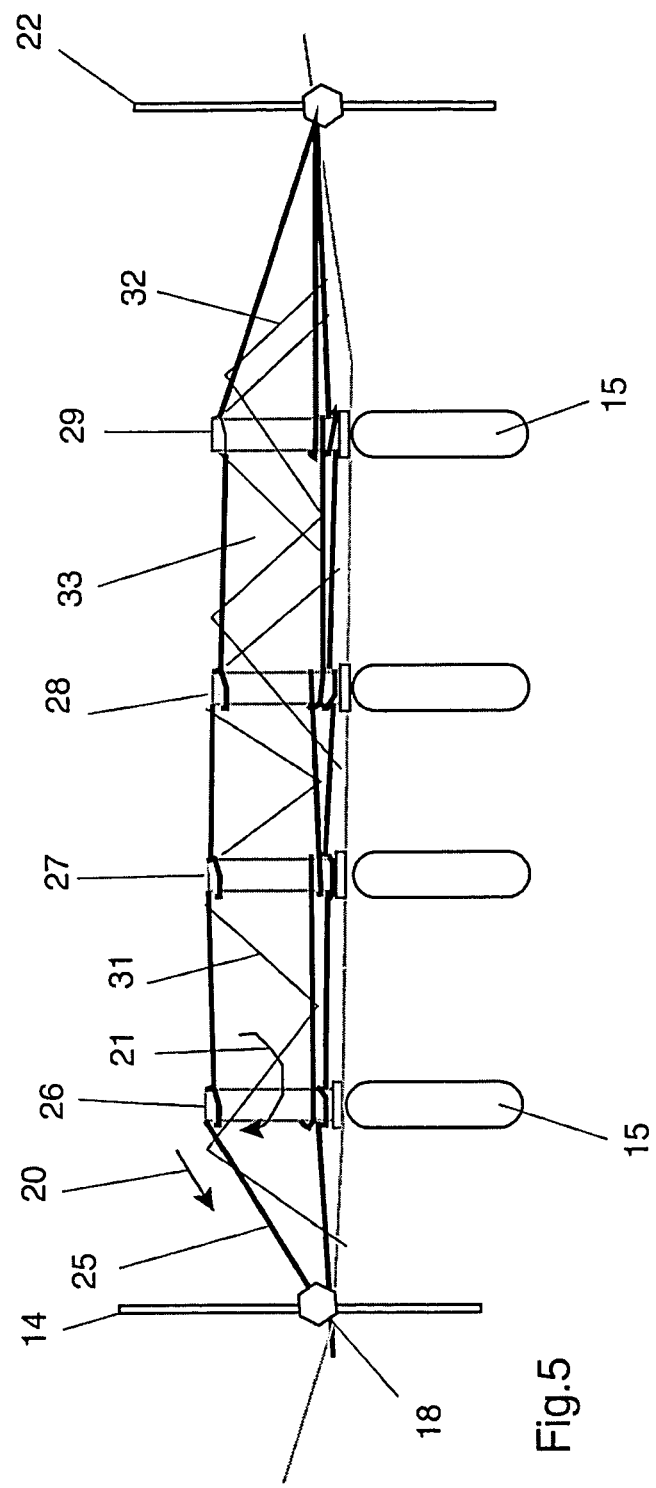

In FIG. 5, a third reinforcement element 25 is fixed to the base of the left-hand tension post 14 provided with retaining means 18. This third element 25 is tensed to join the apex 26 of the nearest implant abutment 16 around which it is wound in the clockwise direction (arrow 21), and so on around the following implant abutment 27, and then the third 28 and fourth 29 abutment and is then brought down to the base of the right-hand tension post 22. The third reinforcement element 25, distally to the most distal left and right implants, is thus inclined by an angle of 30° to 45° with the base elements.

The third reinforcement element 25 is then photo-polymerized and remains in the determined position to act as main upper brace for the framework of the armature.

Additional reinforcement elements 31, 32 are wound off from the bases of the framework with a path encompassing the upper brace and the base decks. These elements 31, 32 act as secondary braces and present a smaller cross-section, for example 0.80 mm.

The winding direction of the reinforcement elements can vary according to the anatomic data.

The secondary braces of the elements 31, 32 perform complementary support of the base elements with ties forming an angle of 10 to 85° with the base elements.

They sequentially encompass the vestibular base element, the upper brace, the lingual or palatine base element, and so on.

The empty spaces 33 are filled with a resin, for example PPMA, of the same nature as the impregnating resin of the fibres constituting the base elements and braces. Filling is performed by means of the pressing or injection techniques known in dental prosthesis laboratories, and the prosthetic teeth are always included in the method by means of known techniques.

In advantageous manner, the tension posts are then released.

The invention claimed is:

1. A dental bridge armature designed to be screw-fastened onto dental implants, said armature being made from composite constituted by fibres and particles, and filled with resin by deposition, pressing or injection, said armature comprising:
reinforcing elements formed by long fibres pre-impregnated with photo-polymerizable resin which are either woven or in bundles, said reinforcing elements being in the form of a fibrous framework, comprising a main brace and base reinforcing elements, all wound around a series of implant abutments screw-fastened onto the implants, and the ends of the main brace are inclined in the direction of the base reinforcing elements, a first reinforcing element being wound around the implant abutments in a clock-wise direction, and a second reinforcing element being wound around the implant abutments in a counter-clockwise direction, wherein the main brace and the base reinforcing elements are wound around the implant abutments at different heights of the implant abutments so as to form a three-dimensional structure.

2. The dental bridge armature according to claim 1, wherein secondary braces are wound around the main brace and the base reinforcing elements.

3. The dental bridge armature according to claim 1, wherein the base reinforcing elements and the braces are tensed from distal tension posts.

4. The dental bridge armature according to claim 2, wherein said braces form an angle comprised between 15° and 85° with the base reinforcing elements.

5. The dental bridge armature according to claim 1, wherein the ends of the main brace are inclined by an angle of 30° to 45° with the base reinforcing elements.

6. The dental bridge armature according to claim 1, wherein the main brace is located on a front side of the implant or on a back side of the implant depending.

7. A method for manufacturing a dental bridge armature according to claim 1, including the following steps:

providing implant abutments, said implant abutments being fixed onto implants;

providing a first tension post and a second tension post, the first tension post and the second tension post being fitted distally to the most distal implants, securing a first reinforcing element and a second reinforcement element to a lower part of the first tension post, the first reinforcement element and the second reinforcement element being successively:
  i. tensed, so as to join the lower part of a nearest implant abutment;
  ii. wound around a base of the implant abutment; and
  iii. polymerized, repeating the steps i, ii and iii until the first reinforcement element and the second reinforcement element finish their path on the lower part of the second tension post, the first reinforcement element and the second reinforcement element forming base reinforcing elements;

securing a third reinforcement element to the lower part of the first tension post, the third reinforcement element being successively:
  iv. tensed, so as to join a superior part of the nearest implant abutment;
  v. wound around the superior part of the implant abutment; and
  vi. polymerized, repeating the steps iv, v and vi until the third reinforcement element finishes its path on the second tension post, the third reinforcement element being fixed to the lower part of the second tension post, the third reinforcement element forming a main brace element, the main brace element and the base reinforcing elements forming a three-dimensional structure;

winding and polymerizing additional reinforcing elements around the base reinforcement elements and around the main brace element, so as to form secondary braces, the base reinforcement elements, the main brace element and the secondary braces forming a fibrous armature;

injecting a coating resin into free spaces of the fibrous armature after polymerization of the first reinforcing element, the second reinforcing element, the third reinforcing element and the additional reinforcing elements, and releasing the first tension post and the second tension post.

8. A dental bridge armature designed to be screw-fastened onto dental implants, said armature being made from composite constituted by fibers and particles, and filled with resin by deposition, pressing or injection, said armature comprising reinforcing elements formed by long fibers pre-impregnated with photo-polymerizable resin which are either woven or in bundles, said reinforcing elements being in the form of a fibrous framework, said fibrous network comprising:

a main brace being wound around a superior part of a series of implant abutments screw-fastened onto the implants; and base reinforcing elements being wound around a lower part of the series of implant abutments screw-fastened onto the implants, such that a first reinforcing element is wound around the implant abutments in a clockwise direction, and a second reinforcing element is wound around the implant abutments in a counter-clockwise direction, the main brace and the base reinforcing elements being located at different heights of the implant abutments, so as to form a three-dimensional structure, the ends of the main brace being inclined in the direction of the base reinforcing elements, so as to be fixed to the base reinforcing elements.

* * * * *